United States Patent
Pürschel

(10) Patent No.: US 6,478,810 B1
(45) Date of Patent: Nov. 12, 2002

(54) TANNING BOOTH

(75) Inventor: Dieter Pürschel, Dortmund (DE)

(73) Assignee: Iris Kopper, Dortmund (DE)

( * ) Notice: Subject to any disclaimer, the term of this patent is extended or adjusted under 35 U.S.C. 154(b) by 42 days.

(21) Appl. No.: 09/655,924

(22) Filed: Sep. 6, 2000

(30) Foreign Application Priority Data

Sep. 15, 1999 (DE) .......................... 199 44 975

(51) Int. Cl.$^7$ ................................................ A61N 5/00
(52) U.S. Cl. ............................................ 607/91; 607/94
(58) Field of Search ......................... 607/91, 94, 95, 607/93, 100, 90, 88; 128/205.26; 600/21

(56) References Cited

U.S. PATENT DOCUMENTS

| 4,205,684 A | * | 6/1980 | Lassy | 607/95 |
| 4,918,319 A | * | 4/1990 | Kruithof | 250/493.1 |
| 5,683,437 A | * | 11/1997 | Doty | 607/88 |
| 5,957,959 A | * | 9/1999 | Rissmaney et al. | 250/494.1 |
| 6,139,568 A | * | 10/2000 | Doty | 250/504 R |

FOREIGN PATENT DOCUMENTS

| DE | 4005677 | * | 8/1991 | 607/94 |
| GB | WO-9217242 | * | 3/1991 | 607/94 |

* cited by examiner

Primary Examiner—Linda C. M. Dvorak
Assistant Examiner—Kenneth Schopfer
(74) Attorney, Agent, or Firm—Friedrich Kueffner

(57) ABSTRACT

A tanning booth has a tanning bed and a horizontally pivotable irradiation cover pivotable into an irradiation position above the tanning bed and pivotable into an access position allowing access to the tanning bed, wherein in the irradiation position the irradiation cover surrounds the tanning bed at least partially. The irradiation cover is shaped as a spherical segment or a cylindrical segment and has a curved inner wall facing the tanning bed, wherein the inner wall has a reflective layer. Irradiation light sources emit light beams onto the reflective layer of the inner wall.

10 Claims, 4 Drawing Sheets

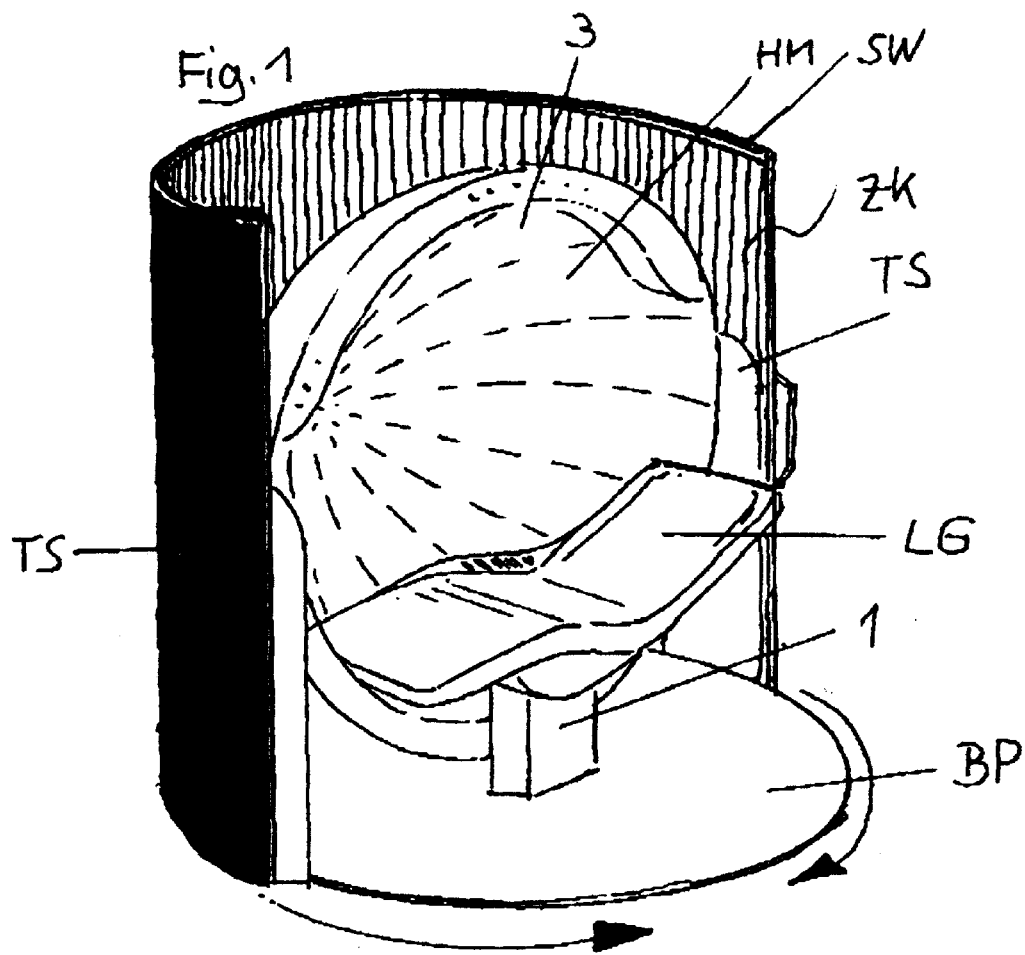
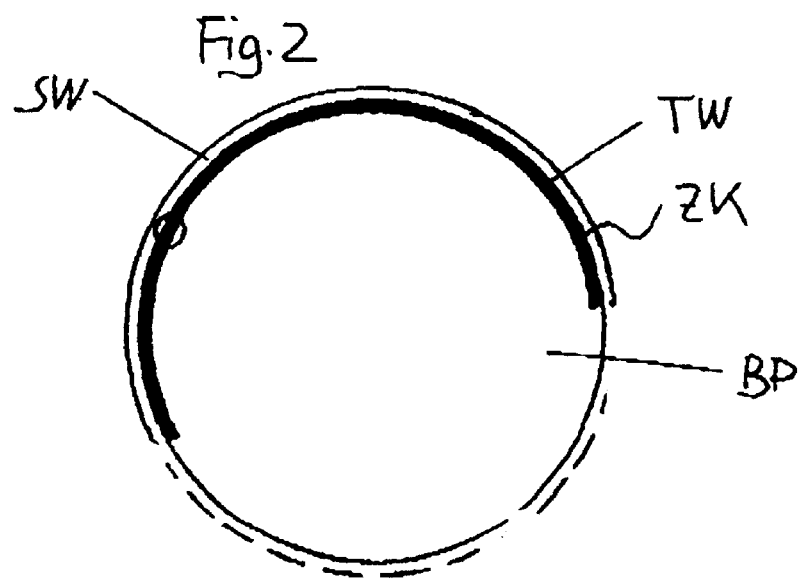

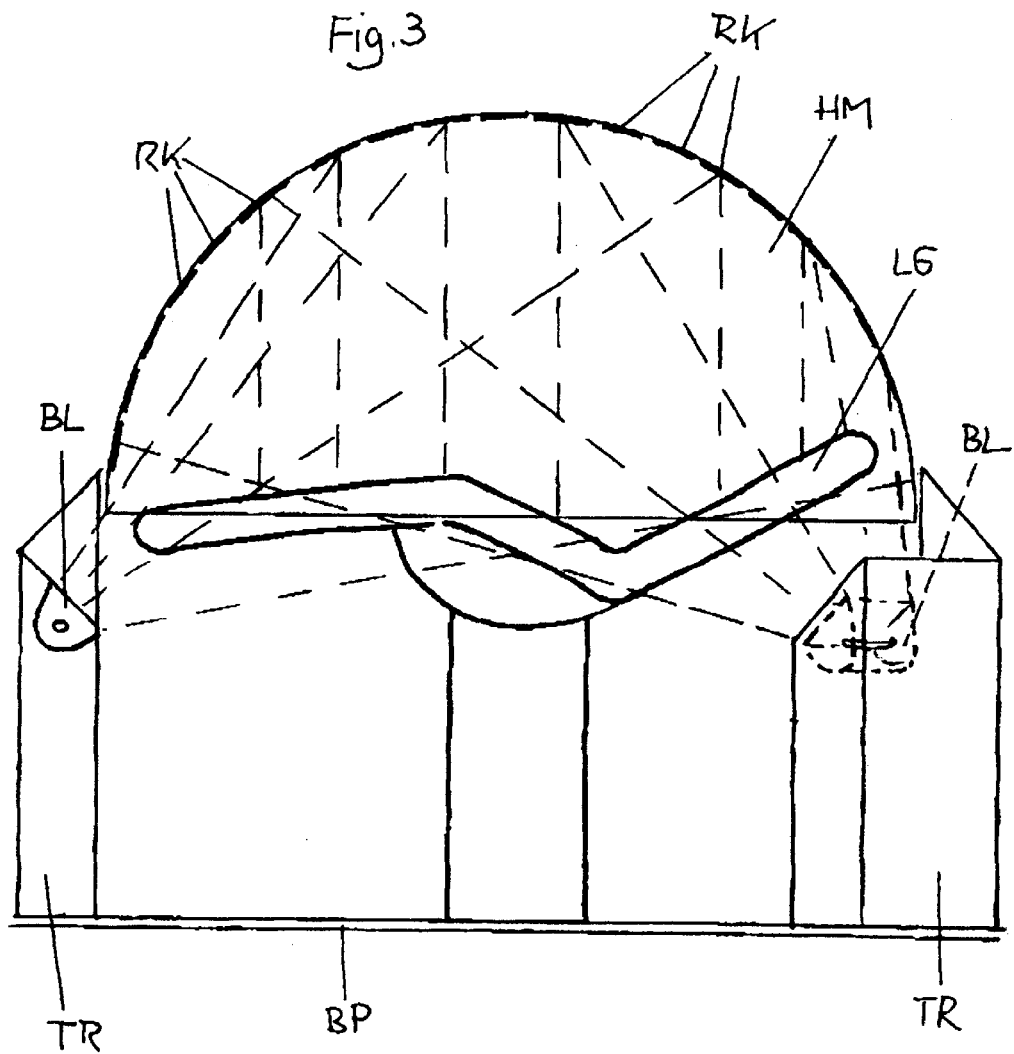

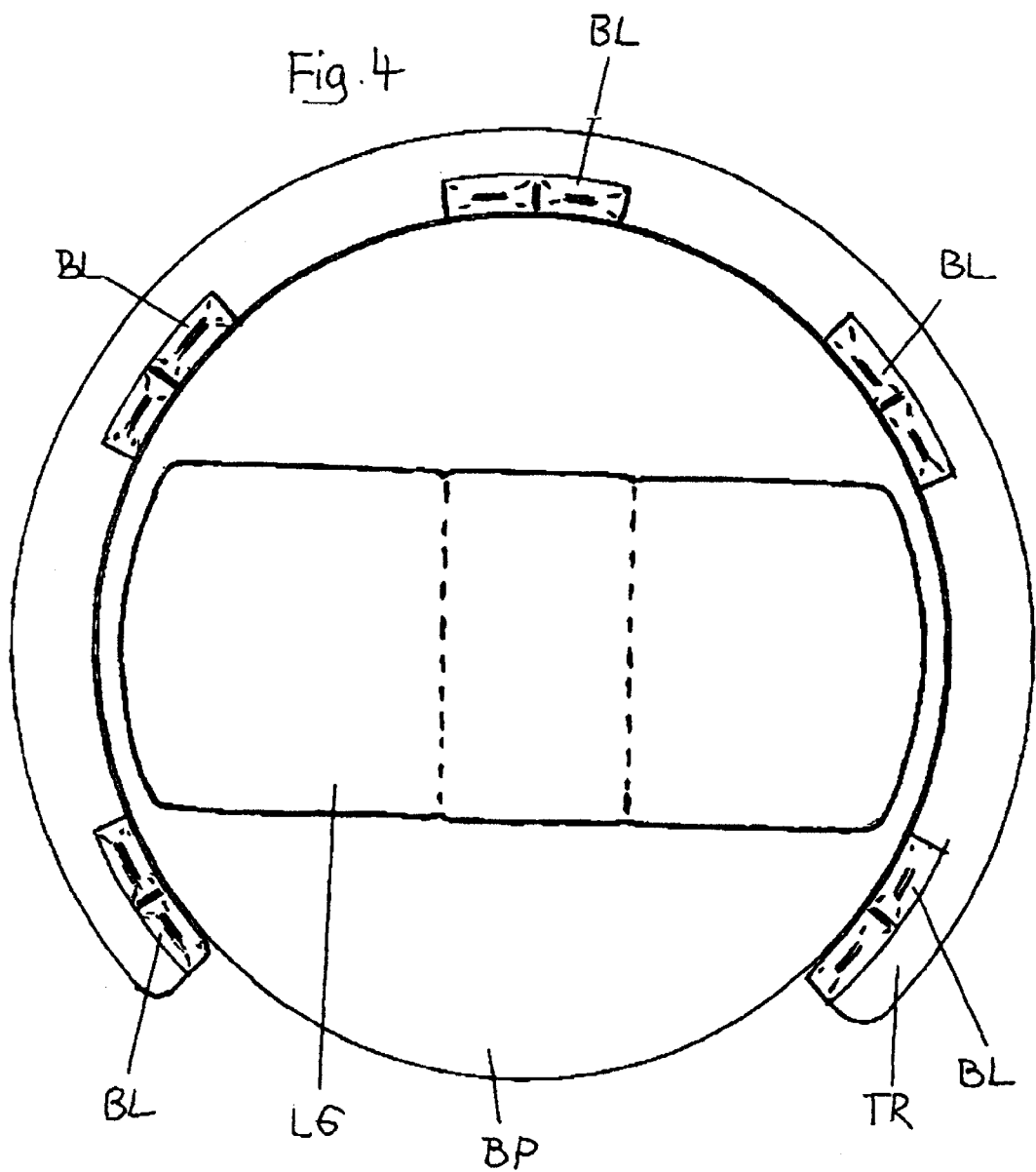

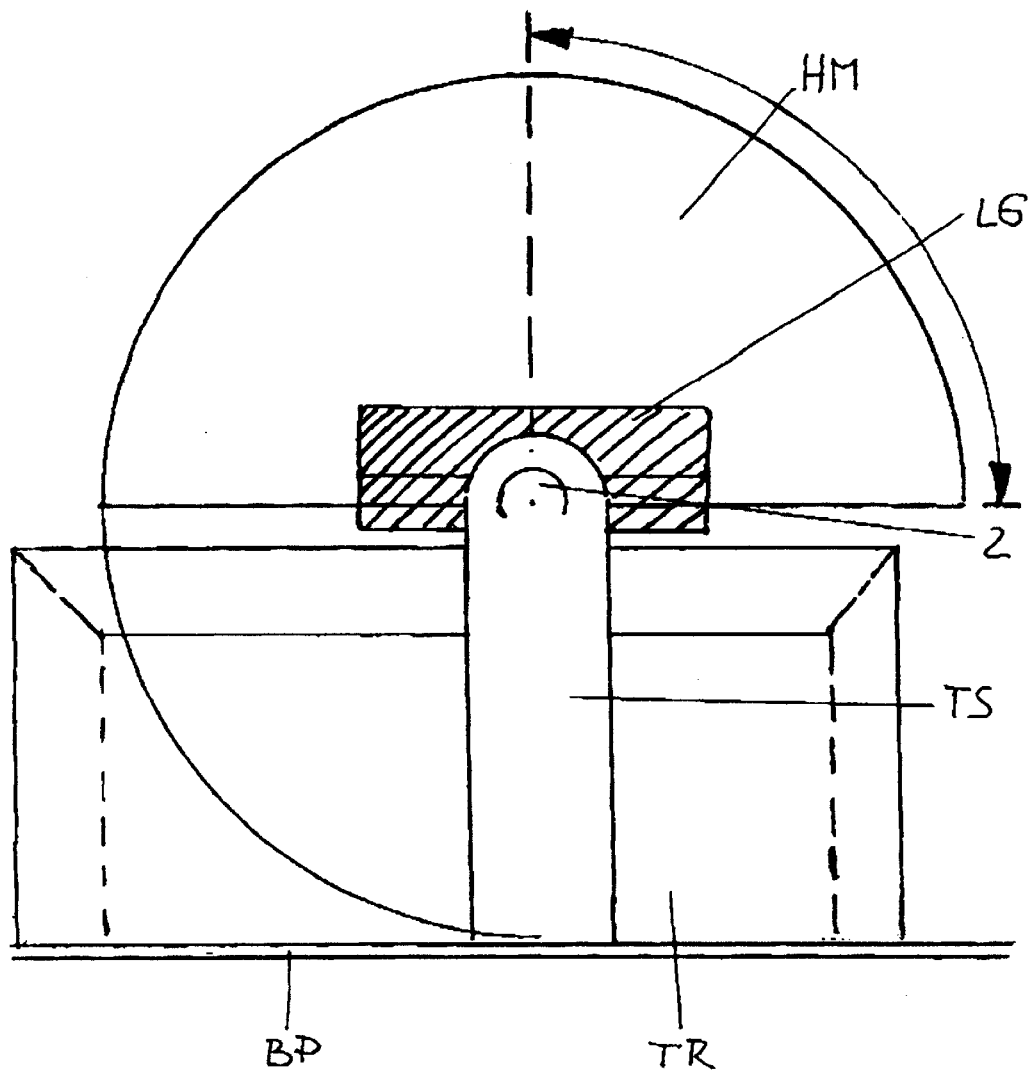

TANNING BOOTH

BACKGROUND OF THE INVENTION

1. Field of the Invention

The invention relates to a tanning booth comprised of a tanning bed, which is positioned on the floor or a bottom plate, for the person to be irradiated and an irradiation cover pivotable about a horizontal axis which can be pivoted from an access position in which the tanning bed is accessible into an irradiation position above the tanning bed wherein the irradiation cover partially surrounds the tanning bed in the irradiation position.

2. Description of the Related Art

Irradiation booths of this kind are known in various embodiments which all have the common disadvantage that, after the irradiation cover has been pivoted into the irradiation positions the person resting on the tanning bed is confined within a very tight space through which vented air flows, wherein the irradiation light sources in the cover are positioned at a relatively small spacing above the body of the person. These conditions, inter alia, are perceived throughout as more or less uncomfortable, especially by persons suffering from claustrophobic conditions, because of the limited freedom of movement, the heat stress, and also the blinding effect of the irradiation light sources.

It has already been suggested to counteract these disadvantages by a configuration of the tanning devices that is open in the upward direction and in which individual irradiation light sources are arranged at a greater spacing above the tanning bed. Also, suggestions are known according to which the beams of the irradiation light sources is not directly guided onto the tanning bed but by means of reflective mirrors.

SUMMARY OF THE INVENTION

It is an object of the present invention to improve a tanning booth of the aforementioned kind such that the irradiation is essentially indirect and causes only minimal heat stress while a considerably increased freedom of movement for the person to be irradiated, even during the irradiation process, is provided.

In accordance with the present invention, this is achieved in that the irradiation cover is formed as a spherical segment or cylinder segment having an inner wall facing the tanning bed which is provided with a reflective layer or a plurality of reflective bodies which can be loaded by the beams of the irradiation light sources positioned within or external to the irradiation cover or/and arranged on its rim portion.

As is furthermore suggested by the invention, the light beams emitted by the irradiation light sources can be bundled and directed onto certain portions of the curved inner wall. The reflective bodies can be comprised of a row of mirror panes with plane or curved mirror surfaces. The mirror panes can be arranged so as to be angularly adjustable and securable. A housing which receives the spherical segment or cylindrical segment is expediently supported on both sides of the opening diameter (opening cross-section) in horizontal pivot bearings.

Moreover, according to the invention the irradiation light sources can be arranged on a support frame in the form of a circular portion open toward the front which support frame, in the irradiation position of the irradiation cover, is positioned at a spacing below the opening cross-section and surrounds the tanning bed.

Finally, the tanning bed, the irradiation cover, and the irradiation light sources can be arranged in a cylindrical enclosure which is open in the upward direction and is comprised of a stationary, upright, approximately semi-cylindrical support wall and an also approximately semi-cylindrical closure wall which is arranged so as to be slidable about the support wall or within the support wall.

BRIEF DESCRIPTION OF THE DRAWING

In the drawing:

FIG. 1 is a perspective view of a tanning booth with a cylindrical enclosure, viewed from the side and from above;

FIG. 2 is a plan view onto FIG. 2 without tanning bed;

FIG. 3 is a front view of FIG. 1 in a schematic representation;

FIG. 4 is a plan view of FIG. 3; and

FIG. 5 is a side view of FIG. 3, also in a schematic representation.

DESCRIPTION OF THE PREFERRED EMBODIMENTS

FIG. 1 shows the tanning bed LG with its support 1 arranged on a bottom plate BP. The tanning bed LG can be lifted, lowered, and pivoted (these functions are not illustrated not shown). This bottom plate BP supports an upwardly open cylinder enclosure ZK which is comprised of an upright approximately semi-cylindrical support wall TW, positioned on the bottom plate BP, and a closure wall SW also approximately semi-cylindrical and slidingly arranged in glide rails about the outer periphery of the support wall TW. Within the semi-cylindrical support wall TW, support beams TS are positioned on the bottom plate BP diametrically opposite one another at the two ends of the tanning bed LG with a spacing to the two ends. Between the support beams TS the irradiation cover HM is pivotably arranged with pivot bearings 2 (see FIG. 5). In the shown embodiment the irradiation cover HM is a semi-sphere. The irradiation cover HM can be pivoted from the open access position, illustrated in FIG. 1, in which the circular opening cross-section is positioned in an approximately vertical plane, into the closed irradiation position, illustrated in FIG. 5, in which the opening cross-section is positioned in an approximately horizontal plane and surrounds the tanning bed LG. A support frame TR which is open to the front extends circularly about the tanning bed LG and about the opening at a spacing below the opening when in its horizontal position. The support frame TR stands on the bottom plate BP and rests against the support wall (FIGS. 3 and 4). At the upper rim of this support frame TR the irradiation light sources BL are positioned in an annular arrangement and at a spacing to one another so as to be directionally adjustable and securable. In the curved inner wall 3 of the irradiation cover HM a plurality of reflective bodies RF is inserted which, when positioned in predetermined reflective angular positions, provide the possibility, as can be seen in FIG. 3, to direct the beams emitted by the irradiation light sources BL in a targeted way and, if desired, in a predetermined bundled way, onto certain portions of the tanning bed LG, respectively, onto corresponding body surfaces of the person to be irradiated. Instead of these reflective bodies forming a reflective layer, the entire inner wall 3 can be provided instead with a reflective coating to form such a reflective layer.

The cylinder enclosure ZK can be accessed in the open position according to FIG. 1, in which the closure wall SW and the irradiation cover HM are pushed back, respectively, pivoted back, without any obstacles being present in the form of lateral walls or other device parts. The person to be irradiated, after having accessed the tanning booth, can now pivot and height-adjust the tanning bed LG into the desired position, also without any interference, and can then lie down on the tanning bed without being impaired by the irradiation cover HM.

After closing the closure wall SW, if desired, also without closing it, and pivoting the irradiation cover HM into the irradiation position, there is ample free space, primarily above the tanning bed LG, and the irradiation can take place almost entirely without blinding effect and with minimal heat stress.

While specific embodiments of the invention have been shown and described in detail to illustrate the inventive principles, it will be understood that the invention may be embodied otherwise without departing from such principles.

What is claimed is:

1. A tanning booth comprising:

a tanning bed;

a horizontally pivotable irradiation cover configured to be pivotable into an irradiation position above the tanning bed and to be pivotable into an access position allowing access to the tanning bed, wherein in the irradiation position the irradiation cover surrounds the tanning bed at least partially;

the irradiation cover being shaped as a spherical segment or a cylindrical segment and having a curved inner wall facing the tanning bed, wherein the inner wall has a reflective layer;

irradiation light sources configured to emit light beams onto the reflective layer of the inner wall, wherein the irradiation light sources are mounted at a spacing away from said tanning bed and below an opening cross-section of the spherical segment or the cylindrical segment in the irradiation position of the irradiation cover.

2. The tanning booth according to claim 1, wherein the reflective layer is comprised of several reflective bodies.

3. The tanning booth according to claim 1, wherein the irradiation light sources are configured to bundle the light beams and to direct the light beams onto certain portions of the inner wall.

4. The tanning booth according to claim 1, wherein the reflective layer is comprised of rows of reflective bodies in the form of mirror panes with curved or plane mirror surfaces.

5. The tanning booth according to claim 4, wherein the mirror panes are configured to be angularly adjustable and securable in a selected angular position.

6. The tanning booth according to claim 1, wherein the irradiation cover comprises a housing and the spherical segment or the cylindrical segment is mounted in the housing, wherein the irradiation cover further comprises horizontal pivot bearings positioned on opposite sides of the opening cross-section of the irradiation cover.

7. The tanning booth according to claim 6, comprising a support frame arranged at a spacing below the opening cross-section of the spherical segment or the cylindrical segment in the irradiation position of the irradiation cover and surrounding at a spacing the tanning bed, wherein the irradiation light sources are mounted on the support frame.

8. The tanning booth according to claim 1, further comprising an upright cylindrical enclosure open in an upward direction, wherein the tanning bed and the irradiation cover are surrounded by the cylindrical enclosure, wherein the cylindrical enclosure comprises an approximately semi-cylindrical, stationary support wall and a slidable, approximately semi-cylindrical closure wall.

9. The tanning booth according to claim 8, wherein the semi-cylindrical closure wall is slidably arranged on an outside periphery of the semi-cylindrical support wall.

10. The tanning booth according to claim 8, wherein the semi-cylindrical closure wall is slidably arranged on an inner periphery of the semi-cylindrical support wall.

\* \* \* \* \*